(12) United States Patent
Tanner et al.

(10) Patent No.: US 6,217,902 B1
(45) Date of Patent: *Apr. 17, 2001

(54) SOFT GELATIN CAPSULES CONTAINING PARTICULATE MATERIAL

(75) Inventors: Keith E. Tanner, Safety Harbor; Gregory A. Schurig, Clearwater, both of FL (US); Frank S. S. Morton, Swindon (GB); Brian R. Pansari, Tampa, FL (US); John L. Cain, Dunedin, FL (US); Rickey S. Shelley, Largo, FL (US); Youchino Wei, Clearwater, FL (US)

(73) Assignee: R. P. Scheier Company, Basking Ridge, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/929,875

(22) Filed: Sep. 15, 1997

Related U.S. Application Data

(63) Continuation of application No. 08/488,905, filed on Jun. 9, 1995, now abandoned.

(51) Int. Cl.$^7$ .................................. A61K 9/64; A61K 9/16
(52) U.S. Cl. ........................ 424/456; 424/490; 424/494
(58) Field of Search .................................. 424/456, 489, 424/490, 464, 480, 494

(56) References Cited

U.S. PATENT DOCUMENTS

| 4,486,412 | 12/1984 | Shah et al. | 424/156 |
|---|---|---|---|
| 5,002,777 | 3/1991 | Cuca | 424/687 |
| 5,472,712 | * 12/1995 | Oshlack et al. | 424/480 |
| 5,672,360 | * 9/1997 | Sacklen et al. | 424/490 |

FOREIGN PATENT DOCUMENTS

WO 94/08576  4/1994  (WO) .

* cited by examiner

Primary Examiner—Thurman K. Page
Assistant Examiner—Blessing Fubara
(74) Attorney, Agent, or Firm—Donald D. Nickey; Steve Sarussi

(57) ABSTRACT

Disclosed are suspensions suitable for encapsulation in gelatin capsules, comprising a solid phase consisting of solid particles having a mean diameter of at least about 149 μm, and a liquid phase capable of suspending the solid phase, the suspension having a predetermined rheology at a temperature suitable for encapsulation into gelatin capsules.

17 Claims, 4 Drawing Sheets

SOFT GELATIN CAPSULES CONTAINING PARTICULATE MATERIAL

This is a continuation of application Ser. No. 08/488,905 filed Jun. 9, 1995.

This application is a continued prosecution application based on a parent filing date of Sep. 15, 1997, now abandoned.

FIELD OF THE INVENTION

The present invention relates to suspensions of solid active agents for encapsulation in gelatin capsules. The invention also relates to gelatin capsules containing a suspension of a solid phase, i.e., particles or beads, in a liquid or semi-solid phase. It further relates to methods and apparatus for the production of soft gelatin capsules containing particulate material in a liquid or semi-solid phase.

DESCRIPTION OF THE RELATED ART

Soft elastic gelatin capsules containing particulate material are now well established as a means for providing a variety of liquid products such as drugs and dietary supplements in a readily ingestible form.

Known apparatus for producing filled gelatin capsules comprises either flat or rotary dies having recesses against which the capsule wall is shaped.

Conventional rotary die encapsulation apparatus can be used to produce soft elastic gelatin capsules containing suspensions of specific viscosities. These suspensions include suspensions of powders in liquids. To achieve trouble-free encapsulation of such suspensions, the suspension system must be pourable and pumpable and preferably homogeneous at a temperature suitable for encapsulation in a gelatin capsule. Furthermore, the particle size of the powders intended for encapsulation in such suspensions must be less than about 120 microns ($\mu$m).

Medicinal products and other active agents are frequently prepared in the form of microbeads. Such microbeads normally have diameters in excess of 180 microns. For example, typical sustained release pharmaceutical microbeads have a diameter of about 900 microns.

Encapsulation of microbeads in excess of about 180 microns using conventional state-of-the-art rotary die encapsulation apparatus produces capsules having many defects. Among the defects are non-uniform distribution of the microbeads in the gelatin capsules. Other more important problems are found during the encapsulation process itself. For example, suspensions of microbeads do not pass through the ports and tubes of the rotary die apparatus without significant and unsuitable levels of "clogging." This is a result of the solid phase separating from the liquid phase. The present invention is designed to overcome the problems with encapsulation of suspensions of microbeads.

SUMMARY OF THE INVENTION

Although conventional rotary die encapsulation apparatus can be used to prepare soft gelatin capsules containing suspensions of solid particulate materials of mean diameters less than 180 $\mu$m, problems arise when the particles have diameters in excess of 180 $\mu$m. The present invention provides a solution to the problems associated with encapsulating microbeads or particles in suspensions.

In yet another aspect, the present invention provides suspensions of solid or particulate active agents, e.g., pharmaceutical agents, suitable for encapsulation in gelatin capsule. The suspensions of pharmaceutical agents may be encapsulated in gelatin capsules for subsequent oral administration. The invention also provides capsules suitable for a variety of non-oral uses.

Accordingly, a broad embodiment of the invention encompasses suspensions of active agents, the suspensions comprising a solid phase and a liquid phase capable of suspending the solid phase for at least a period of time sufficient to allow encapsulation into a gelatin capsule. The solid phase may comprise particles or beads having a mean diameter of at least about 149 $\mu$m. The solid phase may also comprise single or multi-component particles having mean diameters of at least about 149 $\mu$m. The inventive suspensions are pumpable at temperatures suitable for encapsulation into gelatin capsules. These suspensions, i.e., gelatin capsule fill materials, can be pumped without sedimentation or separation and without clogging of the various parts in a rotary die apparatus.

The invention further encompasses gelatin capsules comprising a fill material where the fill material is a suspension comprising a liquid phase and a solid phase.

The invention also encompasses methods and apparatus for preparing such gelatin capsules. The apparatus comprises a rotary die encapsulation machine modified to allow a suspension or slurry to be encapsulated without clogging of the various ports, tubes, and injection wedges. The apparatus alternatively may comprise a flat die encapsulation machine or a suitable liquid fill 2 piece hardshell encapsulation machine.

The invention thus provides gelatin capsules having particles or beads that may be visible within the capsule and readily discernable from the liquid phase.

The inventive gelatin capsules are also more tamper resistant since such capsules that have been tampered with or adulterated may be more readily distinguished.

The invention further provides gelatin capsules capable of releasing active agents at various predetermined times. For example, the liquid phase may comprise at least one active agent dissolved in the liquid phase available for immediate release while the solid phase may comprise a single agent or a plurality of different active agents formulated to have release profiles different from each other and from the agents in the liquid phase. Thus, the solid phase may comprise at least two different types of particles or beads, each containing a different active product.

DETAILED DESCRIPTION OF THE INVENTION

Figure 1:
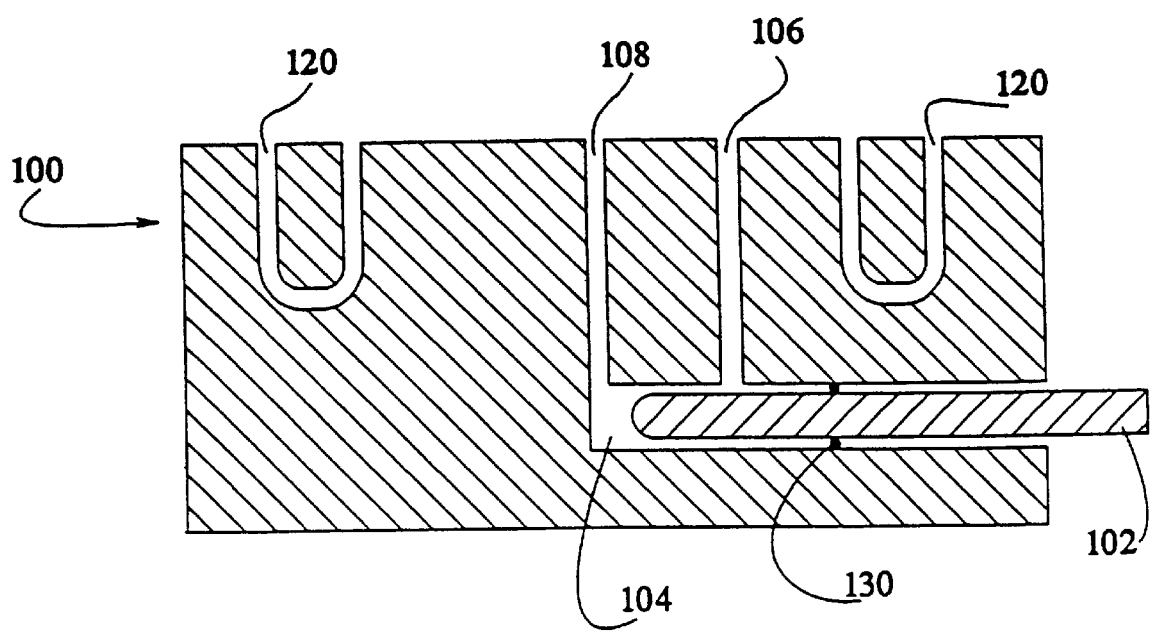
FIG. 1 is a cross-section through a dosing pump for use with a rotary die encapsulation machine.

As used herein, "pumpable" means a slurry that may be pumped by a positive displacement pump.

As used herein, "pourable" means that a material is capable of flowing down a 1" diameter pipe under the effect of gravity at a specified manufacturing temperature.

As used herein, "suspension" means a solid phase, i.e., particles or beads, stably and uniformly distributed in a liquid phase for a minimum predetermined period of time. Thus, the suspension may, after a certain time period, separate resulting in sedimentation of the solid phase.

As used herein, "particle" means any solid material containing one or more components.

The invention provides suspensions, semi-solid formulations, and heterogeneous mixtures comprising a solid phase contained in a liquid or semi-solid phase. The physical state of the mixture, i.e, whether the mixture is heterogeneous, semi-solid, or liquid, depends on the temperature of the mixture. By heterogenous mixture is meant a non-uniform mixture of solid and liquid phases.

The solid phase comprises a material that is insoluble or of limited solubility in the liquid phase. The solid phase may comprise any of a variety of active agents, e.g., pharmaceutical agents; fragrances; flavoring agents; surfactants such as soaps; adhesives; diagnostic agents such as radiolabelled markers; fertilizers; herbicides; pesticides; cosmetics including, for example, quaternary ammonium conditioning agents; oils; skin nutrients; and metabolites.

The invention is particularly suitable for suspending and encapsulating various pharmaceutical agents or pharmaceutically acceptable salts of the pharmaceutical agents. Representative non-toxic pharmaceutically acceptable salts include salts of acids such as, for example, hydrochloric, phosphoric, hydrobromic, sulfuric, sulfinic, formic, toluene sulfonic, hydroiodic, acetic, trifluoroacetic and the like. Those skilled in the art will recognize a wide variety of non-toxic pharmaceutically acceptable addition salts.

The solid phase may comprise a single active agent or may comprise a mixture of different active agents formulated into beads or particles. Thus, the solid phase may comprise one or more active agents in different types of particles or beads, or may comprise a single kind of bead or particle containing one or more active agents.

The solid phase may consist of microbeads having a solid exterior. Such microbeads may include a solid or a liquid core. Suitable microbeads may be formed by spray coating, coacervation, spray drying, or by other means known to those skilled in the art. The microbeads may be any of a variety of combinations of component materials. The microbeads may comprise core, active and coating materials; typically these materials are present in the microbeads as layers of the component materials. The microbeads must be prepared such that the bead exterior does not interact adversely with the liquid phase or the surrounding gelatin capsule. Thus, the bead exterior will not affect the stability of (1) the liquid phase or its various components, or (2) the stability or integrity of the gelatin shell. For example, microbeads can be prepared according to methods known to those skilled in the art to include an exterior coating comprising a cellulose polymer. Such a material is effective at preventing interaction between the active agent in the encapsulated bead and the liquid phase or gelatin capsule.

The microbeads or particles suitable for use in the invention have mean diameters of from about 149 $\mu$m to 2500 $\mu$m. More preferably, the beads have mean diameters of from about 200 $\mu$m to 1300 $\mu$m. Particularly preferred beads have mean diameters of from about 600 $\mu$m to 1300 $\mu$m.

The solid particles of the invention include any solid material of one or more components. Where the particles comprise a plurality of components, these components may be uniformly dispersed in the particles, i.e., a homogenous mixture. Alternatively, the particles may be heterogeneous mixtures.

An example of a solid pharmaceutical agent suitable for use in the inventive suspensions is sustained release pharmaceutical beads having a mean diameter of about 900 $\mu$m.

Preferred solid phase beads or particles have surfaces that are substantially free from irregularities that contribute to and allow clogging of ports and tubes within the encapsulation apparatus.

The amount of the solid phase in the suspensions of the invention is from about 0.5 to 70%, preferably 15 to 50%, and more preferably 15 to 40% by weight based on the total weight of the suspension. Particularly preferred suspensions comprise from about 30 to 40% by weight of solid phase based on the weight of the suspension.

Suitable liquid phases are those that are capable of suspending the solid phase without separating for at least a period of time sufficient to allow encapsulation of the suspension in gelatin capsules. This capability is only required of the liquid phase at the specific temperature at which the suspension will be pumped through the encapsulation machine. Thus, the suspensions may separate and become non-uniform, i.e., heterogeneous, mixtures of solid and liquid phases over extended periods of time, or at elevated temperatures.

Consequently, the suspensions are designed to have a rheology that is suitable under the conditions at which the suspension will be filled into gelatin capsules. The suspension may also be designed to have a rheology which achieves a particular physical state for the suspension after encapsulation. This result can be obtained in a variety of ways.

For example, where the suspension is intended to behave as a "gel" or viscous material at ambient temperature after encapsulation, the liquid phase can be selected such that it is of a viscosity at the manufacturing temperature that allows effective suspending of the solid phase while having a rheology not detrimental to pumping through a rotary die apparatus. Such a fill material may be pumped at ambient temperature, about 20° C. to 22° C.

Alternatively, the required rheology may be attained by selecting a liquid phase that is a liquid at a first temperature and a semi-solid at a second temperature. The first temperature may be higher than the second temperature or, alternatively, the first temperature may be lower than the second temperature. Further, liquid phase may be selected to be of such a rheology or viscosity that they are not pumpable at ambient temperature but require heating to become pumpable. Such a liquid phase would essentially be a solid at ambient temperature. Such materials should become pumpable at a temperature of no more than 45° C., since higher temperatures are detrimental to the encapsulation process. Materials that are semi-solid at a higher temperature and liquid at a lower temperature include certain compounds that gel when heated. In a preferred embodiment, the fill material is pumped and encapsulated at from about −15 to 18° C., preferably 0 to 15° C. in order to maintain the solid phase suspended uniformly in the semi-solid or liquid phase. Such a liquid phase is semi-solid at a temperature of about −15 to 18° C. and a liquid at about 20° C. A fill material prepared with this semi-solid phase, upon warming to ambient temperature, becomes liquid. Thus, a gelatin capsule can be provided where the fill material includes a solid phase that, when tilted or rotated 180° vertically, moves at a predetermined rate through the liquid phase under the influence of gravity. For example, a suspension can be prepared in which microbeads or particles pass from one end of a gelatin capsule to the other through the liquid phase in from about 2 to 15 seconds.

Thus, liquid phases that are pumpable at ambient, subambient, and above-ambient temperatures are suitable for use in the invention. Thus, these liquid phases, at a certain temperature, are of a rheology suitable for suspending microbeads at the desired temperature. Such rheology may be characterized in either of two ways. First, as discussed above, the medium may be of a viscosity sufficient to provide at least temporary, homogeneous suspension of the solid phase, i.e., capable of suspending the solid phase for at least a period of time sufficient to allow encapsulation of the suspension in gelatin capsules.

Second, the liquid phase may be a low viscosity fluid with a yield value sufficient to suspend microbeads. By "yield value" is meant the energy input required of a system to cause the system to flow. Thus, the liquid phase may essentially be a liquid at the encapsulation temperature, but will have a yield value sufficient to suspend the solid phase at least during the encapsulation process.

For highly viscous liquids elevated temperatures can be used to improve flow, providing temperatures of above 45° C. are not exceeded.

Such liquid phases are those that are pumpable by a positive displacement pump. Such liquid phases may be prepared using one or more of the following hydrophilic and lipophilic liquids: fractionated coconut oil, coconut oil, propylene glycol dicaprylate/dicaprate, glyceryl caprylate/caprate, polyethylene glycol 400, polyethylene glycol 600, polyethylene glycol 3350, polyethylene glycol 8000 solutions of polyvinyl pyrrolidone, propylene glycol, carbomer 934, soya bean oil, hydrogenated palm oil, sesame oil, 75% maltitol syrup, polysorbate 80, mixtures thereof, and mixtures thereof with water. Certain of the forgoing materials are liquids only above ambient temperature or when combined with other liquid components.

Other suitable liquids can be selected from the following:
1. Vegetable oils and fats.
2. Mineral oils and waxes.
3. Ester oils and waxes.
4. Silicone oils and waxes.
5. Ethoxylated vegetable oils and fats.
6. Non-ionic surfactants, e.g. sorbitan esters, polyoxyethylene alkyl ethers, polyoxyethylene castor oil derivatives, polyoxyethylene sorbitan fatty acid esters, polyoxyethylene stearates, and poloxamers.
7. Concentrated sugar solutions e.g. maltitol syrup, sorbitol syrup, sucrose syrup, glucose syrup.
8. Polyethylene glycols of various molecular weights.
9. Triacetin.
10. Propylene carbonate.
11. Aliphatic alcohols having from 1 to 6 carbon atoms.
12. Polyhydric alcohols.
13. Glycofuranol.
14. Water.
15. Polyvinyl pyrrolidone (as a component of aqueous and non aqueous solutions).
16. Starches and polysaccharides (in aqueous or non-aqueous solutions or suspensions).

In certain embodiments, the liquid phase will further comprise a suspending agent. Representative suspending agents are silicones, fats, waxes, cellulose derivatives such as, example, hydroxyethyl cellulose, hydroxymethyl cellulose, methyl cellulose, starch, or hydrolyzed starch, gums such as, for example, guar gum, xanthan gum, alginic gum, arabic, or acacia, synthetic polymer thickeners such as carbopol and polyvinyl pyrrolidone, fumed silica, and clays such as bentonite.

Preferred liquid phases are those that are capable of lubricating the beads to prevent clogging of ports and tubes in the encapsulation apparatus.

The preferred liquids used in the liquid phase must not adversely interact or affect the stability of the actives within the bead or particle or affect the physical integrity of the bead or particle. Additionally the compatibility of the liquid phase should be such that only small to negligible amounts of active should migrate or leech from the bead or particle into the liquid phase. If it is known that active(s) will migrate from the solid phase to the liquid phase, the liquid phase should be chosen such that the solubility of the active(s) is sufficiently low in the liquid to prevent complete loss of the active from the solid phase. Thus, an equilibrium of active agent(s) is established between the two phases.

A preferred liquid phase comprises fractionated coconut oil (commercially available as Captex 355) and coconut oil (commercially available as Pureco 76). Various combinations of coconut and fractionated coconut oil were prepared and their suspending properties determined at various sub-ambient temperatures. Another preferred liquid phase comprises a 50:50 (w/w) blend of Softigen 767 (PEG-6 capric glycerides, commercially available from Huls America) and Capmul MCM (glyceryl caprylate/caprate, commercially available from Capital City).

The suitability of various suspensions with respect to encapsulation in softgel capsules may be determined by the following method. A sample is placed into a 10 ml syringe at the desired pumping/encapsulation temperature having an injection orifice of about 2 to 10 times the mean diameter of the particles or microbeads. The slurry is forced out of the syringe and the orifice monitored for blockage. Tests were repeated four times and the results are shown below in Table 1.

The following formulations were analyzed using the above test.

| COMPONENT | % W/W |
|---|---|
| FORMULATION 1 | |
| Fractionated Coconut Oil | 63.00 |
| Fumed Silicon Dioxide | 4.00 |
| 900 μm Microbeads (average diameter) | 33.0 |
| FORMULATION 2 | |
| Fractionated Coconut Oil | 60.97 |
| Fumed Silicon Dioxide | 2.68 |
| Polysorbate 80 | 3.35 |
| 900 μm Microbeads | 33.00 |
| FORMULATION 3 | |
| PEG 400 | 60.38 |
| PEG 3350 | 4.49 |
| PEG 8000 | 2.13 |
| 900 μm MICROBEADS | 33.00 |
| FORMULATION 4 | |
| PEG 400 | 56.95 |
| CARBOPOL 934 | 1.34 |
| WATER | 5.36 |
| PROPYLENE GLYCOL | 3.35 |
| 900 μm MICROBEADS | 33.00 |
| FORMULATION 5 | |
| PEG 400 | 37.52 |
| WATER | 3.89 |

-continued

| COMPONENT | % W/W |
|---|---|
| PROPYLENE GLYCOL | 2.41 |
| POLY VINYL PYRROLIDONE K30 | 23.18 |
| 900 µm MICROBEADS | 33.00 |
| FORMULATION 6 | |
| PEG 400 | 61.00 |
| PROPYLENE GLYCOL | 3.00 |
| POLY VINYL PYRROLIDONE K90 | 3.00 |
| 900 µm MICROBEADS | 33.00 |

TABLE 1

| FORMULATION NUMBER[1] | SYRINGE BLOCKAGE (NO./4 TESTS) |
|---|---|
| FORMULATION 1 | 4 OUT OF 4 TESTS BLOCKED |
| FORMULATION 2 | 4 OUT OF 4 TESTS BLOCKED |
| FORMULATION 3 | 2 OUT OF 4 TESTS BLOCKED |
| FORMULATION 4 | 3 OUT OF 4 TESTS BLOCKED |
| FORMULATION 5 | NO BLOCKAGE |
| FORMULATION 6 | NO BLOCKAGE |

[1]Formulation numbers correspond to the formulations described above.

Examples of suitable liquid phases that are soft semi-solids suitable for both suspending of the solid phase and for pumping with the rotary die encapsulation machine are shown below.

| | | Physical state | | | | |
|---|---|---|---|---|---|---|
| | | Ambient | 10° C. | 5° C. | −10° C. | cloud point ° C. |
| Captex 335, % by weight | Pureco 76, % by weight | | | | | |
| 80 | 20 | clear liquid | fluid semi-solid | soft semi-solid | soft waxy solid | 13 |
| 70 | 30 | clear liquid | soft semi-solid | soft semi-solid | hard waxy solid | 16 |
| Softigen 767, % by weight | Capmul MCM, % by weight | | | | | |
| 50 | 50 | clear liquid | fluid semi-solid | soft waxy solid | hard waxy solid | 16 |

The fill materials, i.e., suspensions of solid phase in liquid phase, are suitable for encapsulation into either hard or soft gelatin capsules.

Encapsulation in hardshell capsules typically involves the use of liquid fill two piece hard shell apparatus with a suitably modified and enlarged dosing mechanism to facilitate the pumping of the suspension of particles or beads. Alternatively, the apparatus may be modified to pre-dose the dry beads into the main body of the hardshell capsule, add the liquid phase, and finally to affix the cap portion to the capsule. Standard hardshell apparatus may also be modified to produce capsules by the latter method. Each apparatus is directed to preparing gelatin capsules where the gelatin capsules comprise an end portion comprising gelatin and a cap portion also comprising gelatin, where the cap portion securely fits over at least a portion of the end portion to form a two piece hard gelatin capsule.

Preferred gelatin capsules according to the invention are soft gelatin capsules. Such capsules are typically prepared employing a rotary die apparatus. Preferably, a premixed fill material is encapsulated according to the rotary die process. Alternatively, the soft gelatin capsules may be filled with a rotary die apparatus modified to include two or more fill nozzles, one or more to dispense the liquid phase and another or others to dispense the solid phase. An example of such a multinozzle apparatus is described in Australian patent application AU-A-67021/86.

Such rotary die apparatus comprises two cylindrical rollers mounted with their longitudinal axes substantially parallel and defining a cavity therebetween. A plurality of recesses are formed in the outer surface of at least one of the rollers, and means are provided for feeding gelatin ribbon to each roller surface and thereby to the cavity. Such apparatus is described in an article entitled "Soft gelatin capsules: a solution to many tableting problems" published in Pharmaceutical Technology in September 1985. The apparatus is also described in a chapter by J. P. Stanley in *Theory and Practice of Industrial Pharmacy*.

According to the invention, a conventional rotary die apparatus is modified for use with suspensions containing a solid phase of particles or microbeads. The modified rotary die apparatus is especially useful in preparing gelatin capsules comprising suspensions of microbeads having mean diameters in excess of about 180 microns, preferably from about 600 to 1300 microns, and most preferably about 900 microns. The modified apparatus is capable of filling soft gelatin capsules with a fill material comprising a solid phase of particles or microbeads and a liquid phase capable of suspending the solid phase for at least a period of time sufficient to allow encapsulation of the fill material into a gelatin capsule. The fill material, of course, is pumpable at a temperature suitable for encapsulation into gelatin capsules.

Figure 2:
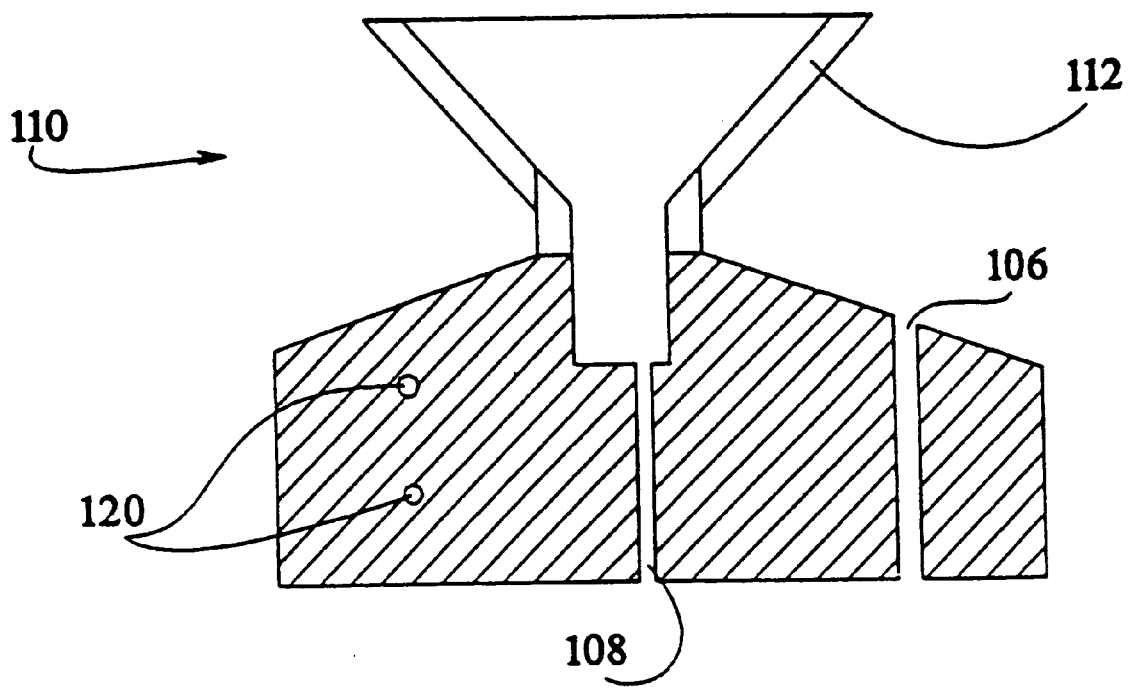
FIG. 2 is cross-section through a hopper for containing the fill material to be encapsulated.
Figure 3:
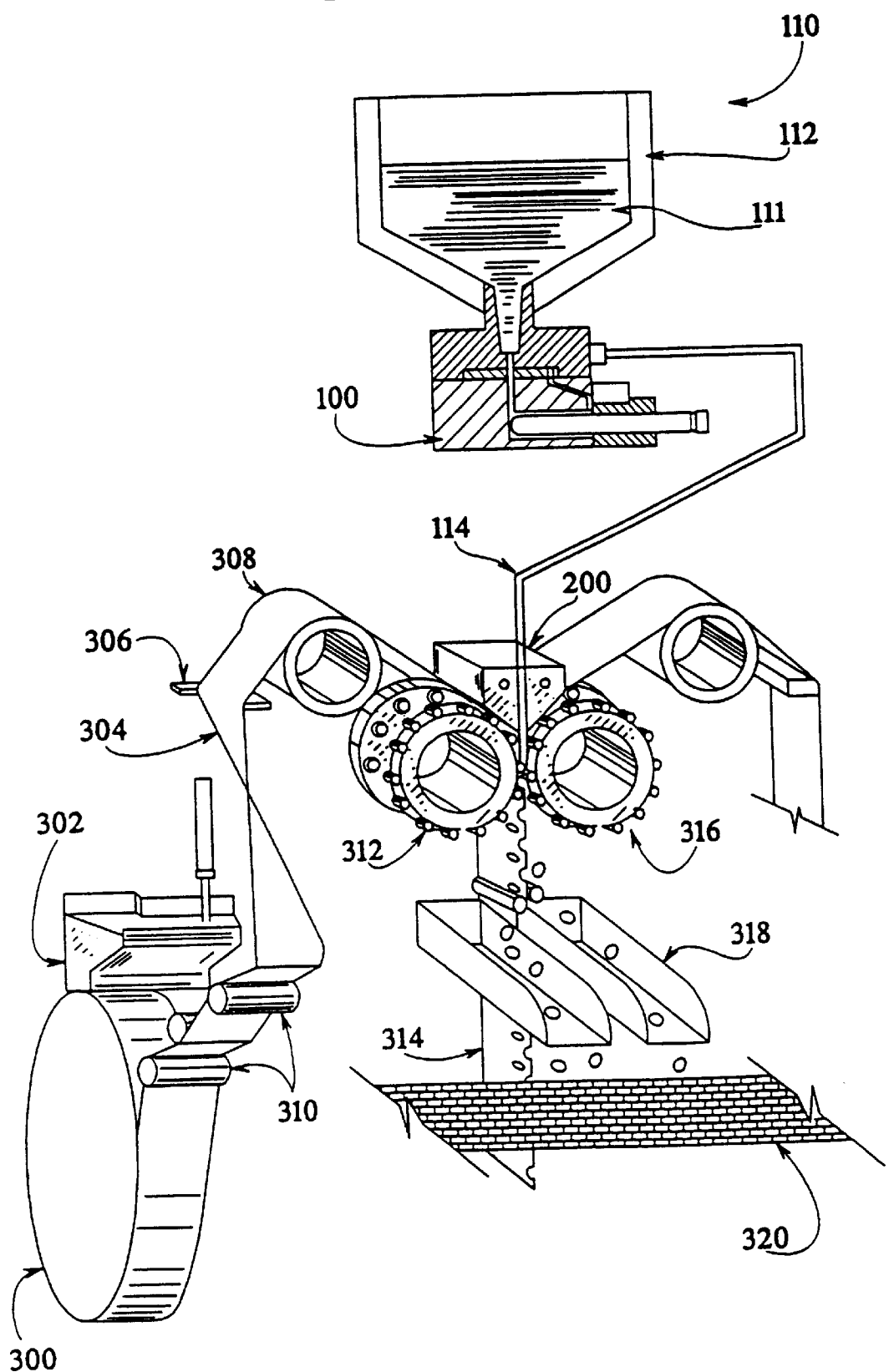
FIG. 3 is a diagram of a rotary die encapsulation apparatus according to the invention.
Figure 4:
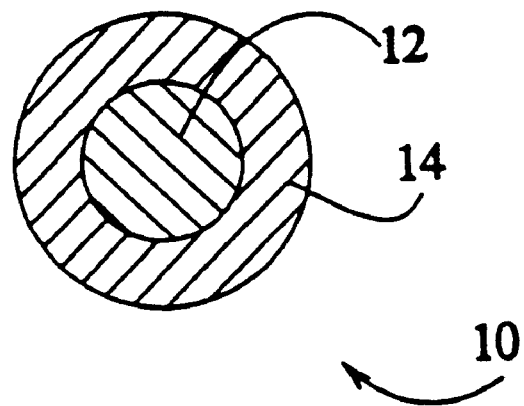
FIG. 4 is a cross-section of a microbead (10) having a core material (12) and an active agent layer (14).

A conventional rotary die apparatus includes a pump 100 (see FIG. 1) that operates by positive liquid displacement. The pump comprises piston 102 that is forced into chamber 104. Chamber 104 is fitted with sleeve 130 and is slightly larger in bore than piston 102 causing fill material to flow out of chamber 104 into discharge or outlet port 106. Chamber 104 is filled with material during the return stroke of piston 102. The return stroke draws material from hopper 110 (see FIG. 2) through inlet port 108 into chamber 104.

In preferred embodiments, inlet port 108 and discharge port 106 have diameters of at least about 2 to 10 times the mean diameter of the particles or microbeads intended for encapsulation. In the modified rotary die apparatus, the ports 106 and 108 are configured to have smooth curves rather than sharp or acute angles in order to minimize constrictions causing clogging of the pump mechanism. Any angles present within ports 106 and 108 are preferably at least about 110° or 120°.

Pump 100 is fabricated to contain at least one, and preferably a plurality of coolant passages 120. Through coolant passages 120 is passed a coolant at a temperature sufficient to maintain the suspension at a temperature desired for encapsulation.

In addition, the modified rotary die apparatus includes a hopper 110 for maintaining the fill material at a predetermined temperature, e.g., from about −15° C. to 18° C.

Preferably, hopper 110 includes a coolant-jacket 112 into which a variety of coolants may be introduced. Among the coolants suitable for use are cooled oils, dry ice-solvent mixtures, aqueous glycolic solutions, and water. The preferred coolant operation temperature is selected to maintain the fill material in a semi-solid state suitable for pumping. A preferred operating temperature is from about 0 to 15° C. A preferred coolant for circulation through the coolant-jacket 112 is a glycolic solution (i.e., water and propylene glycol).

Figure 5:
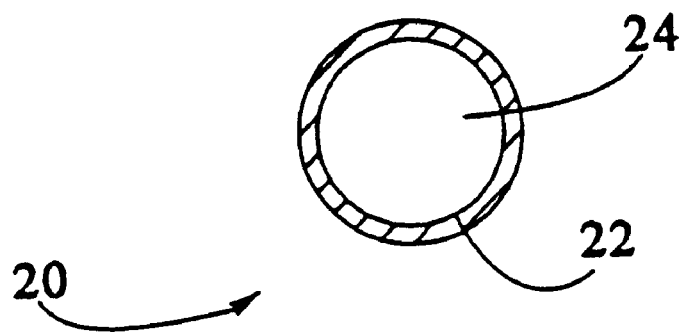
FIG. 5 is a cross-section of a microbead (20) having a barrier coating (22) encapsulating or surrounding a liquid active agent (24).

Suitable materials for preparing the tubular leads 114 extending from ports 106 to wedge 200 (see FIG. 5) include stainless steel and nylon, preferably pharmaceutical grade nylon. Preferred materials for the tubular leads insulate the fill material during transfer from the hopper to the wedge 200.

Any tubes or parts within wedge 200 have diameters of at least about 2 to 10 times the mean diameter of the solid phase intended for encapsulation. Such tubes or ports have angles of preferably at least about 100° or 120°. Further wedge 200 is provided with a means for insulating the cold fill material from the heated edges of the wedge to prevent melting of the fill material. However, where cooling is not required to maintain the suspension, no insulation is needed in wedge 200 and the ports and tubes in wedge 200 must only have the required diameters and angles.

The gelatin capsules prepared using the modified rotary die apparatus comprise a soft gelatin shell and a fill material encapsulated within the shell comprising a solid phase in a liquid phase.

All documents, e.g., patents and journal articles, cited above or below are hereby incorporated by reference in their entirety.

One skilled in the art will recognize that modifications may be made in the present invention without deviating from the spirit or scope of the invention. The invention is illustrated further by the following examples which are not to be construed as limiting the invention or scope of the specific procedures described herein.

EXAMPLE 1

Capsules prepared at ambient temperatures can be produced using a suitably modified rotary die apparatus. The modifications include alterations to the fill dosing mechanism to enable smooth passage of the fill material without clogging of the various ports and tubes by the solid phase. Examples of fill materials are listed in table 2 and formulations 8 to 12. Formulations 8 to 12 are prepared by first producing a homogeneous mixture of the liquid(s) and optional suspending agent(s) and then blending into that mixture the solid phase in the form of microbeads or particles to achieve a uniform mixture.

TABLE 2

| INGREDIENT | FILL MATERIAL (mg/capsule) | | | |
|---|---|---|---|---|
| Polyethylene Glycol 400 | 832.0 | 1087.0 | 979.5 | 867.88 |
| Propylene Glycol | 41.0 | 53.6 | 48.25 | 42.76 |
| Providone K90 | 41.0 | 53.6 | 48.25 | 42.76 |
| 900 µm Microbeads | 450.0 | 132.8 | 269.0 | 407.70 |
| Fill weight | 1346.0 | 1328.0 | 1345.0 | 1362.0 |

| COMPONENT | % by weight |
|---|---|
| FORMULATION 8 | |
| SOYA BEAN OIL (CAPTEK 355) | 50.0 |
| HYDROGENATED PALM OIL | 20.0 |
| 800 µm MICROBEADS | 30.0 |
| FORMULATION 9 | |
| SESAME OIL | 66.0 |
| CABOSIL | 4.0 |
| POLYSORBATE 80 | 10.0 |
| 1200 µm MICROBEADS | 20.0 |
| FORMULATION 10 | |
| HYDROXYETHYL CELLULOSE | 1.0 |
| MALTITOL SYRUP 75% | 69.0 |
| 1100 µm MICROBEADS | 30.0 |
| FORMULATION 11 | |
| POLYSORBATE 80 | 10.0 |
| FRACTIONATED COCONUT OIL | 73.0 |
| CARBOXYMETHYL CELLULOSE | 2.0 |
| 900 µm MICROBEADS | 15.0 |
| FORMULATION 12 | |
| POLYETHYLENE GLYCOL 600 | 67.5 |
| POLYETHYLENE GLYCOL 3350 | 5.0 |
| POLYETHYLENE GLYCOL 8000 | 2.5 |
| 900 µm MICROBEADS | 25.0 |

EXAMPLE 2

Soft gelatin capsules are prepared using a rotary die apparatus having a hopper with a coolant jacket, a cooled pump, and an injection wedge adapted as described above. The pump inlet and outlet ports allow smooth passage of the fill without clogging by the solid phase. The hopper and pump portions of the apparatus are cooled to temperatures in the region of 0 to 14° C. with a mixture of water/propylene glycol. Gelatin capsules are filled with fill materials according to formulations 13 to 15. Formulations 13 to are prepared by first preparing the liquid phase blend and adding to the blend the solid phase, i.e., the pharmaceutical agent in the form of microbeads. The blend is deaerated under vacuum and chilled to the required processing temperature while agitating the mixture with a low shear mixing device to achieve a homogenous suspension of the solid phase in the semi-solid liquid.

| INGREDIENT | mg/softgel |
|---|---|
| FORMULATION 13 | |
| FRACTIONATED COCONUT OIL (CAPTEX 355) | 442.0 |
| COCONUT OIL (PURECO 76) | 110.5 |
| 1300 µm MICROBEADS | 297.5 |
| FILL WEIGHT | 850.0 |
| FORMULATION 14 | |
| CAPMUL MCM | 292.5 |
| SOFTIGEN 767 | 292.5 |
| 1200 µm BEADS | 315.0 |
| FILL WEIGHT | 900.0 |
| FORMULATION 15 | |
| FRACTIONATED COCONUT OIL | 405.0 |
| COCONUT OIL | 67.5 |
| CAPMUL MCM | 202.5 |
| 1200 µm BEADS | 225.0 |
| FILL WEIGHT | 900.0 |

From the foregoing, it will appreciated that although specific embodiments of the invention have been described herein for purposes of illustration, various modifications may be made without deviating from the spirit or scope of the invention.

What is claimed is:

1. A suspension of an active agent suitable for encapsulation in soft gelatin capsules, comprising a solid phase consisting of beads containing said active agent and having a solid exterior and a mean diameter of from about 149 μm to about 2500 μm, and a liquid phase suspending the solid phase substantially uniformly at a predetermined temperature, the suspension being pumpable and suitable for encapsulation into said soft gelatin capsule at said predetermined temperature; and wherein said beads comprise a coating effective to prevent interaction of the active agent with the liquid phase or the soft gelatin capsule.

2. A suspension according to claim 1, wherein the beads have a mean diameter of from about 180 to 2500 μm.

3. A suspension according to claim 2, wherein the beads have a mean diameter of from about 200 to 1300 μm.

4. A suspension according to claim 3, wherein the beads comprise pharmaceutical agents or salts thereof and the beads have a mean diameter of from about 600 to 1300 82 m.

5. A suspension according to claim 1, wherein the amount of beads in the suspension is from about 0.5 to 70% by weight of the suspension.

6. A suspension according to claim 5, wherein the amount of beads in the suspension is from about 15 to 50% by weight of the suspension.

7. A suspension according to claim 6, wherein the amount of beads in the suspension is from about 15 to 40% by weight of the suspension.

8. A suspension according to claim 7, wherein the liquid phase comprises a liquid selected from the group consisting of vegetable oils and fats, mineral oils and waxes, ester oils and waxes, silicone oils and waxes, ethoxylated vegetable oils and fats, non-ionic surfactants, aqueous sugar solutions, polyethylene glycols, triacetin, propylene carbonate, aliphatic alcohols having from 1 to 6 carbon atoms, polyhydric alcohols, glycofuranol, water, aqueous and non-aqueous solutions of polyvinyl pyrrolidone, aqueous solutions of polysaccharides, and mixtures thereof.

9. A suspension according to claim 7, wherein the liquid phase comprises a liquid and usually a suspending agent selected from the group consisting of fractionated coconut oil, coconut oil, propylene glycol dicaprylate/dicaprate, glyceryl caprylate/caprate, polyethylene glycol 400, polyethylene glycol 600, polyethylene glycol 3350, polyethylene glycol 8000, polyvinyl pyrrolidone, propylene glycol, carbomer 934, soya bean oil, hydrogenated palm oil, sesame oil, cabosil, hydroxyethyl cellulose, 75% maltitol syrup, polysorbate 80, carboxymethyl cellulose, mixtures thereof, and mixtures thereof with water.

10. A suspension according to claim 1 encapsulated within a gelatin capsule.

11. A suspension of an active agent suitable for encapsulation in soft gelatin capsules, comprising a solid phase of solid particles having a men diameter of about 149 μm to about 2500 μm, and a liquid phase capable of suspending the solid phase for at least a period of time sufficient to allow encapsulation into said soft gelatin capsules, the suspension being pumpable at a temperature suitable for encapsulation into gelatin capsules and wherein said solid particles comprise a coating effective to prevent interaction of the active agent with the liquid phase or the soft gelatin capsule.

12. A suspension according to claim 11, wherein the particles have a mean diameter of from about 180 to 2500μm.

13. A suspension according to claim 12, wherein the amount of the particles in the suspension is from about 0.5 to 70% by weight of the suspension.

14. A soft gelatin capsule comprising a suspension of a solid phase in a liquid phase, the solid phase consisting of encapsulated beads having a mean diameter of from about 149 μm to 2500 μm, wherein said beads comprise a coating effective to prevent interaction of the active agent with the liquid phase or the soft gelatin capsule.

15. A soft gelatin capsule comprising:

(a) a gelatin shell formed from two gelatin sheets;

(b) a fill contained witin the gelatin sheets; and (c) particles contained within the fill, the fill having a pumpable state at a formation temperature and holding the particles in a consistent suspension in the pumpable state to provide a predetermined quantity range of thee particles between the two gelatin sheets during formation of the gelatin shell, and the fill releasing the particles from the suspension at ambient temperature, the beads migrating through the fill under the effect of gravity under ambient temperature and wherein said beads comprise a coating effective to prevent interaction of the active agent with the liquid phase or the soft gelatin capsule.

16. A suspension according to claim 1, wherein said predetermined temperature is about 15° C.

17. A suspension according to claim 1, wherein said beads flow within said gelatin capsule under gravity at about 20° C.

* * * * *